US00PP23968P2

(12) United States Plant Patent
Beekenkamp

(10) Patent No.: US PP23,968 P2
(45) Date of Patent: Oct. 8, 2013

(54) ***ASTER* PLANT NAMED 'BKATRRV'**

(50) Latin Name: *Aster novi-belgii*
Varietal Denomination: BKATRRV

(75) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 93 days.

(21) Appl. No.: 13/373,732

(22) Filed: Nov. 28, 2011

(51) Int. Cl.
*A01H 5/00* (2006.01)

(52) U.S. Cl.
USPC ..... Plt./355

(58) Field of Classification Search
USPC ..... Plt./355
See application file for complete search history.

*Primary Examiner* — June Hwu
(74) *Attorney, Agent, or Firm* — C. A. Whealy

(57) ABSTRACT

A new and distinct cultivar of *Aster* plant named 'BKATRRV', characterized by its broadly upright and uniformly mounded plant habit; freely branching growth habit; uniform and freely flowering habit; and large daisy-type inflorescences with purple-colored ray florets.

2 Drawing Sheets

Botanical designation: *Aster novi-belgii.*
Cultivar denomination: 'BKATRRV'.

BACKGROUND OF THE INVENTION

The present invention relates to a new and distinct cultivar of *Aster* plant, botanically known as *Aster novi-belgii* and hereinafter referred to by the name 'BKATRRV'.

The new *Aster* plant is a product of a planned breeding program conducted by the Inventor in Maasdijk, The Netherlands. The objective of the breeding program was to develop new freely-branching container-type *Aster* plants with uniform plant habit and attractive inflorescence coloration.

The new *Aster* plant originated from an open-pollination in July, 2007 in Maasdijk, The Netherlands of a proprietary selection of *Aster novi-belgii* identified as code number 1001056, not patented, as the female, or seed, parent with an unknown selection of *Aster novi-belgii*, as the male, or pollen, parent. The new *Aster* plant was discovered and selected by the Inventor as a single flowering plant within the progeny of the stated open-pollination in a controlled environment in Maasdijk, The Netherlands in July, 2008.

Asexual reproduction of the new *Aster* plant by vegetative tip cuttings was first conducted in Maasdijk, The Netherlands in November, 2008. Asexual reproduction by cuttings has shown that the unique features of this new *Aster* plant are stable and reproduced true to type in successive generations.

SUMMARY OF THE INVENTION

Plants of the new *Aster* plant have not been observed under all possible environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'BKATRRV'. These characteristics in combination distinguish 'BKATRRV' as a new and distinct *Aster* plant:

1. Broadly upright and uniformly mounded plant habit.
2. Freely branching growth habit.
3. Uniform and freely flowering habit.
4. Large daisy-type inflorescences with purple-colored ray florets.

Plants of the new *Aster* differ from plants of the female parent selection in the following characteristics:

1. Inflorescences of plants of the new *Aster* are fuller than inflorescences of plants of the female parent selection.
2. Inflorescences of plants of the new *Aster* flower have larger discs than inflorescences of plants of the female parent selection.
3. Plants of the new *Aster* and the female parent selection differ slightly in ray floret color.

Plants of the new *Aster* can be compared to plants of *Aster* 'Crown Fortuna', not patented. In side-by-side comparisons conducted in Maasdijk, The Netherlands, plants of the new *Aster* differed from plants of 'Crown Fortuna' in the following characteristics:

1. Plants of the new *Aster* were more uniformly mounded than plants of 'Crown Fortuna'.
2. Leaves of plants of the new *Aster* were narrower than leaves of plants of 'Crown Fortuna'.
3. Inflorescences of plants of the new *Aster* had larger discs than inflorescences of 'Crown Fortuna'.

BRIEF DESCRIPTION OF THE PHOTOGRAPHS

The accompanying photographs illustrate the overall appearance of the new *Aster* plant showing the colors as true as it is reasonably possible to obtain in colored reproductions of this type. Colors in the photographs may differ slightly from the color values cited in the detailed botanical description which accurately describe the colors of the new *Aster* plant.

The photograph on the first sheet comprises a side perspective view of a typical flowering plant of 'BKATRRV' grown in a container.

The photograph on the second sheet are close-up views of the upper and lower surfaces of typical leaves and typical inflorescences of 'BKATRRV'.

DETAILED BOTANICAL DESCRIPTION

The aforementioned photographs and following observations and measurements describe plants grown during the late summer in 15-cm containers in a glass-covered greenhouse in Maasdijk, The Netherlands and grown under environmental conditions and cultural practices which approximate those generally used in commercial container *Aster* production. During the production of the plants, day and night temperatures ranged from 18° C. to 19° C. Plants were pinched 24 days after planting and were eleven weeks old when the photographs and the description were taken. In the following description, color references are made to The Royal Horticultural Society Colour Chart, Fifth Edition, except where general terms of ordinary dictionary significance are used.

Botanical classification: *Aster novi-belgii* 'BKATRRV'.

Parentage:

*Female, or seed, parent.*—Proprietary selection of *Aster novi-belgii* identified as code number 1001056, not patented.

*Male, or pollen, parent.*—Unknown selection of *Aster novi-belgii*, not patented.

Propagation:

*Type.*—Terminal vegetative cuttings.

*Time to initiate roots, summer.*—About 10 to 14 days at temperatures of about 19° to 20° C.

*Time to initiate roots, winter.*—About 14 to 16 days at temperatures of about 19° to 20° C.

*Time to produce a rooted young plant, summer.*—About three weeks at temperatures of about 19° C. to 20° C.

*Time to produce a rooted young plant, winter.*—About three to four weeks at temperatures of about 19° C. to 20° C.

*Root description.*—Medium in thickness, fibrous; white in color.

*Rooting habit.*—Moderately freely branching; medium density.

Plant description:

*Plant shape and habit.*—Herbaceous daisy-type potted *Aster*; broadly upright with lateral branches somewhat outwardly spreading; inverted triangle with uniformly mounded crown.

*Branching habit.*—Strong and freely branching growth habit with about four lateral branches per plant; pinching enhances lateral branch development.

*Plant height.*—About 13.9 cm.

*Plant width.*—About 18.6 cm.

*Lateral branches.*—Length: About 7.8 cm. Diameter: About 2 mm. Internode length: About 8 mm. Strength: Strong. Angle: Upright to about 35° from vertical. Texture: Pubescent. Color: Close to N137B.

Foliage description:

*Arrangement.*—Alternate, simple; sessile.

*Length.*—About 8.9 cm.

*Width.*—About 1.5 cm.

*Shape.*—Narrowly elliptic to oblanceolate.

*Apex.*—Narrowly acute.

*Base.*—Cordate, amplexicaul.

*Margin.*—Entire to finely serrate.

*Venation.*—Pinnate.

*Texture, upper and lower surfaces.*—Glabrous; slightly rugose.

*Color.*—Developing leaves, upper surface: Close to N137A. Developing leaves, lower surface: Close to 137A. Fully expanded leaves, upper surface: Darker than between N137A and 147A; venation, close to N137B. Fully expanded leaves, lower surface: Close to N137A; venation, close to 146A to 146B.

Inflorescence description:

*Appearance.*—Daisy-type inflorescence form with narrowly oblanceolate-shaped ray floret; inflorescences borne uniformly on terminals above and beyond the foliar plane; disk and ray florets arranged acropetally on a capitulum.

*Fragrance.*—None detected.

*Natural flowering season.*—Under natural conditions, plants flower from midsummer into the autumn in The Netherlands; plants begin to flower about five weeks after planting.

*Inflorescence longevity of the plant.*—Inflorescences maintain good substance and color for about two weeks; inflorescences persistent.

*Quantity of inflorescences.*—Freely flowering habit with about 60 inflorescences developing per plant.

*Inflorescence bud.*—Height: About 4 mm. Diameter: About 4 mm. Shape: Globular. Color: Close to 138C; towards the base, close to 143C.

*Inflorescence size.*—Diameter: About 2.9 cm. Depth (height): About 1.4 cm. Diameter of disc: About 1.1 cm. Receptacle height: About 1 mm. Receptacle diameter: About 2 mm. Receptacle color: Close to 145C.

*Ray florets.*—Length: About 1.4 cm. Width: About 3 mm. Shape: Narrowly oblanceolate. Apex: Obtuse. Base: Cuneate. Margin: Entire. Texture, upper and lower surfaces: Smooth, glabrous; longitudinally ribbed. Orientation: Initially upright, then about 70° from vertical. Number of ray florets per inflorescence: About 30 arranged in about two whorls. Color: When opening, upper surface: Between 72B and 77B. When opening, lower surface: Close to 77C. Fully opened, upper surface: Between 72B and 77B; color becoming closer to N81B with development. Fully opened, lower surface: Close to 77C; color becoming closer to N81C to N81D with development.

*Disc florets.*—Quantity per inflorescence: About 50. Length: About 7 mm. Diameter: About 2 mm. Shape: Tubular, elongated; apices, acute. Texture, inner and outer surfaces: Smooth, glabrous. Color, when opening and fully opened, inner and outer surfaces: Close to 155A.

*Phyllaries.*—Number of phyllaries per inflorescence: About 60 arranged in about four whorls. Length: About 5 mm. Width: About 1 mm. Shape: Lanceolate. Apex: Narrowly acute. Base: Cuneate. Margin: Entire. Texture, upper and lower surfaces: Smooth, glabrous. Color, upper surface: Close to 143A. Color, lower surface: Close to 143B.

*Peduncles.*—Length, terminal peduncle: About 3 mm. Length, fourth peduncle: About 7 mm. Diameter: About 1 mm. Angle: Upright to about 40° from vertical. Strength: Strong, flexible. Texture: Smooth, glabrous. Color: Close to 137C.

*Reproductive organs.*—Androecium: Present on disc florets only. Quantity of stamens per floret: Five. Filament length: About 2 mm. Filament color: Close to 145C. Anther shape: Obovate. Anther length: About 1 mm. Anther color: Close to 13C. Pollen amount: Scarce. Pollen color: Close to 22D. Gynoecium: Present on ray and disc florets. Quantity of pistils per floret: One. Pistil length: About 4.5 mm. Stigma shape: Bi-parted. Stigma color: Close to 150D. Style length: About 3.5 mm. Style color: Close to 150D. Ovary color: Close to 145A.

*Seeds and fruits.*—Seed and fruit production have not been observed on plants of the new *Aster.*

Disease & pest resistance: Resistance to pathogens and pests common to *Asters* has not been observed on plants of the new *Aster.*

Garden performance: Plants of the new *Aster* have been observed to have good garden performance and to tolerate temperatures ranging from 8° C. to about 30° C.

It is claimed:

1. A new and distinct *Aster* plant named 'BKATRRV' as illustrated and described.

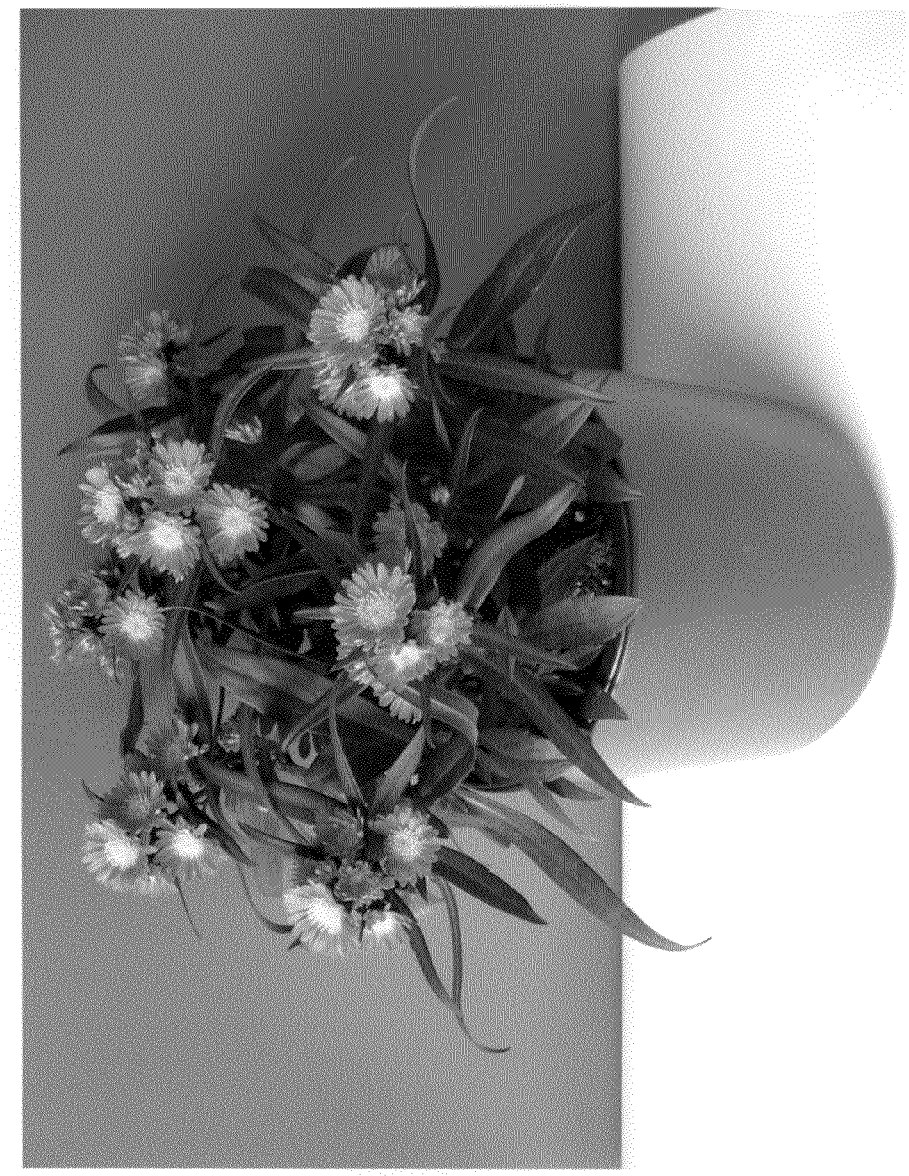

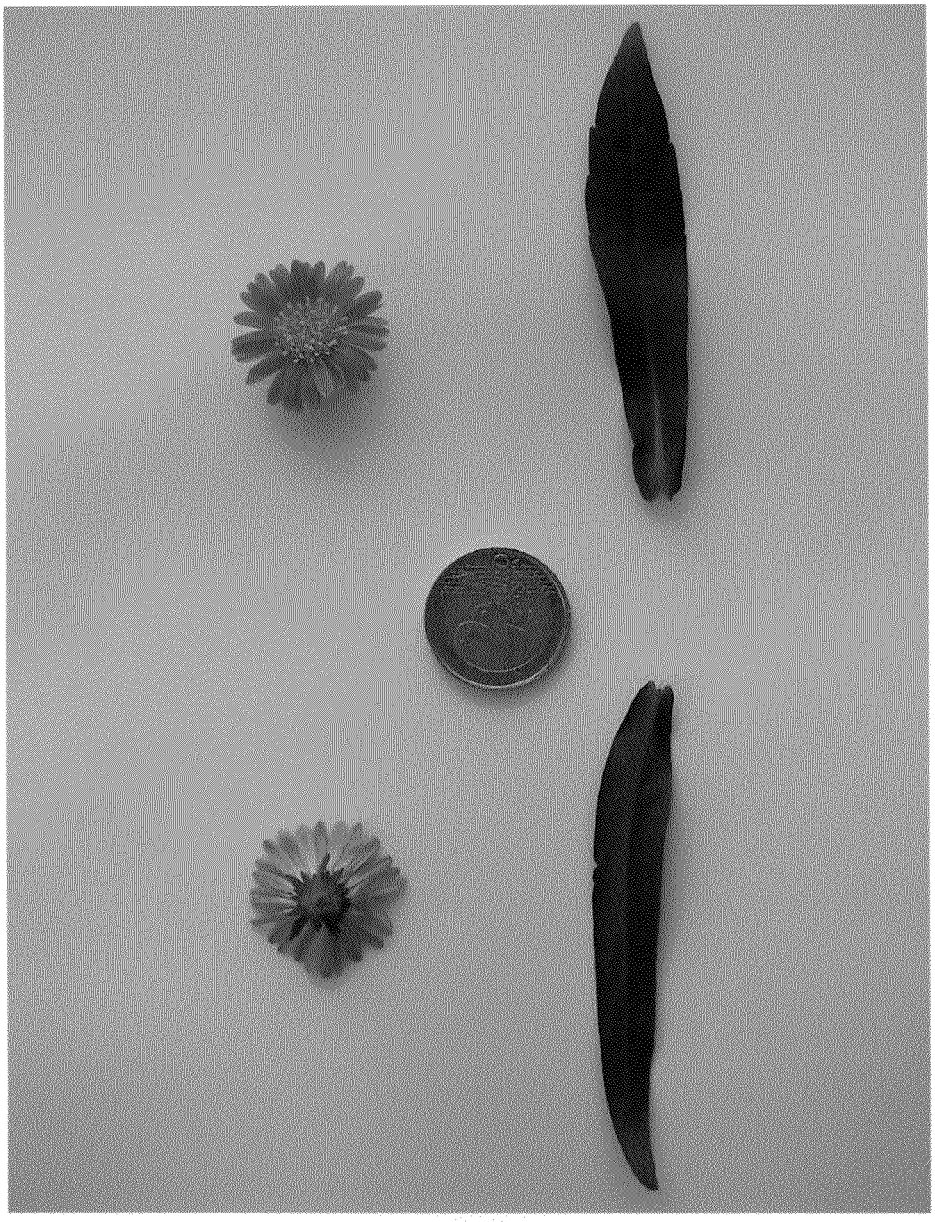

* * * * *